US008758247B2

United States Patent
Kojima

(10) Patent No.: US 8,758,247 B2
(45) Date of Patent: Jun. 24, 2014

(54) ULTRASOUND DIAGNOSTIC APPARATUS AND ULTRASOUND IMAGE PRODUCING METHOD

(75) Inventor: Tetsuya Kojima, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 45 days.

(21) Appl. No.: 13/362,757

(22) Filed: Jan. 31, 2012

(65) Prior Publication Data
US 2012/0232391 A1 Sep. 13, 2012

(30) Foreign Application Priority Data
Mar. 10, 2011 (JP) ................................ 2011-052700

(51) Int. Cl.
*A61B 8/14* (2006.01)
(52) U.S. Cl.
USPC ........... 600/437; 600/443; 600/440; 600/441; 600/459
(58) Field of Classification Search
None
See application file for complete search history.

(56) References Cited

U.S. PATENT DOCUMENTS

| 6,122,538 | A * | 9/2000 | Sliwa et al. | 600/407 |
| 2010/0049046 | A1 * | 2/2010 | Peiffer et al. | 600/443 |
| 2010/0168576 | A1 | 7/2010 | Poland et al. | |

FOREIGN PATENT DOCUMENTS

| JP | 05-245140 | 9/1993 |
| JP | 10-108864 | 4/1998 |
| JP | 2000-107176 | 4/2000 |
| JP | 2006-095071 | 4/2006 |
| JP | 2010-528696 | 8/2010 |
| JP | 2010-274067 | 12/2010 |

OTHER PUBLICATIONS

Japanese Official Action—2011-052700—Feb. 12, 2013.

* cited by examiner

*Primary Examiner* — Long V. Le
*Assistant Examiner* — Farshad Negarestan
(74) *Attorney, Agent, or Firm* — Young & Thompson

(57) ABSTRACT

An ultrasound diagnostic apparatus includes a plurality ultrasound probes, an apparatus body for producing an ultrasound image based on the reception data obtained by one of the ultrasound probes, a connection selector for selectively switching a connection between the ultrasound probes and the apparatus body, an interruption detector for detecting interruption of ultrasound examination, and a controller for causing the apparatus body to display a selection screen for selecting one of the ultrasound probes to be subsequently used when the interruption detector detects interruption of ultrasound examination, wherein when an operator selects one of the ultrasound probes to be subsequently used from the displayed selection screen, the controller controls the connection selector to connect the selected ultrasound probe with the apparatus body.

11 Claims, 4 Drawing Sheets

ULTRASOUND DIAGNOSTIC APPARATUS AND ULTRASOUND IMAGE PRODUCING METHOD

BACKGROUND OF THE INVENTION

The present invention relates to an ultrasound diagnostic apparatus and an ultrasound image producing method and particularly to an ultrasound diagnostic apparatus wherein the connection between a diagnostic apparatus body and one of a plurality of ultrasound probes can be switched.

Conventionally, ultrasound diagnostic apparatus using ultrasound images are employed in medicine. In general, this type of ultrasound diagnostic apparatus comprises an ultrasound probe having a built-in transducer array and an apparatus body connected to the ultrasound probe. The ultrasound probe transmits an ultrasonic beam toward the inside of a subject's body, receives ultrasonic echoes from the subject, and the apparatus body electrically processes the reception signals to produce an ultrasound image.

This type of ultrasound diagnostic apparatus use different sorts of ultrasound probes depending on the diagnosis conditions to meet different diagnosis conditions, and this increases workflow. Efforts are made to improve the workflow by connecting the apparatus body and a plurality of ultrasound probes and selectively switching the connection between an apparatus body and one of a plurality of ultrasound probes through a connection selector.

To switch the connection using the connection selector, the operator operates the apparatus body, for example, to display a selection screen on a monitor showing ultrasound probes for the operator to choose one to use next that meets the diagnosis conditions. Upon the selection, the connection selector, instructed to switch the connection, breaks the connection between the apparatus body and the ultrasound probe connected therewith and connects the apparatus body to an ultrasound probe now selected by the operator. Still further efforts have been made in recent years to improve the workflow as regards the switching by the connection selector.

JP 05-245140 A, for example, proposes an ultrasound diagnostic apparatus in which the ultrasound probes are each provided with a touch sensor, so that when the operator holds an ultrasound probe the operator wishes to use next with a hand, its touch sensor is activated, and the apparatus body is automatically connected to the ultrasound probe whose touch sensor has been activated.

SUMMARY OF THE INVENTION

The above apparatus described in JP 05-245140 A, permitting automatic connection between the apparatus body and the ultrasound probe to be used next, saves the operator the step of operating the apparatus body to have the selection screen displayed on the monitor and selecting an ultrasound probe use next.

However, given automatic switching of the connection between the ultrasound probe and the apparatus body effected upon the detection by the sensor, there is a possibility of the connection being switched automatically as the sensor detects a touch not intended by the operator. In general, to switch the connection between the ultrasound probes and the apparatus body, all the connections between the probes and the apparatus body need to be rewired, making switchover of the connection without interruption of the operation difficult, and hence consuming much time to switch the connection from one selected against the operator's intention to another.

An object of the present invention is to eliminate the above problems associated with the prior art and provide an ultrasound diagnostic apparatus and an ultrasound image producing method reducing the possibility of the connection being switched against the operator's intention while reducing the workflow as regards the switching of the connection between the ultrasound probe and the apparatus body.

An ultrasound diagnostic apparatus according to the present invention comprises:

a plurality of ultrasound probes for transmitting an ultrasonic beam toward a subject and receiving ultrasonic echoes from the subject to produce reception data;

an apparatus body for producing an ultrasound image based on the reception data obtained by one of the ultrasound probes and displaying the produced ultrasound image;

a connection selector for selectively switching a connection between the ultrasound probes and the apparatus body;

an interruption detector for detecting interruption of ultrasound examination; and a controller for causing the apparatus body to display a selection screen for selecting one of the ultrasound probes to be subsequently used when the interruption detector detects interruption of ultrasound examination, wherein when an operator selects one of the ultrasound probes to be subsequently used from the displayed selection screen, the controller controls the connection selector to connect the selected ultrasound probe with the apparatus body.

An ultrasound image producing method according to the present invention comprises the steps of:

connecting one of a plurality of ultrasound probes used for examination to an apparatus body through a connection selector for selectively switching a connection between the ultrasound probes and the apparatus body;

transmitting an ultrasonic beam from the one of the ultrasound probes connected to the apparatus body toward a subject;

producing reception data by the one of the ultrasound probes connected to the apparatus body and having received ultrasonic echoes from the subject;

producing an ultrasound image based on the produced reception data;

displaying the produced ultrasound image;

detecting interruption of ultrasound examination;

displaying a selection screen for selecting one of the ultrasound probes to be subsequently used when interruption of ultrasound examination is detected; and controlling the connection selector to connect the selected ultrasound probe with the apparatus body when an operator selects one of the ultrasound probes to be subsequently used from the displayed selection screen.

BRIEF DESCRIPTION OF THE DRAWINGS

FIG. 7 is a flow chart representing the operation related to production of an interrupt signal in Embodiment 2.

FIG. 8 is a flow chart representing the operation related to production of an interrupt signal in a variation of Embodiment 2.

DETAILED DESCRIPTION OF THE INVENTION

Embodiments of the present invention will now be described below based on the appended drawings.

Figure 1:
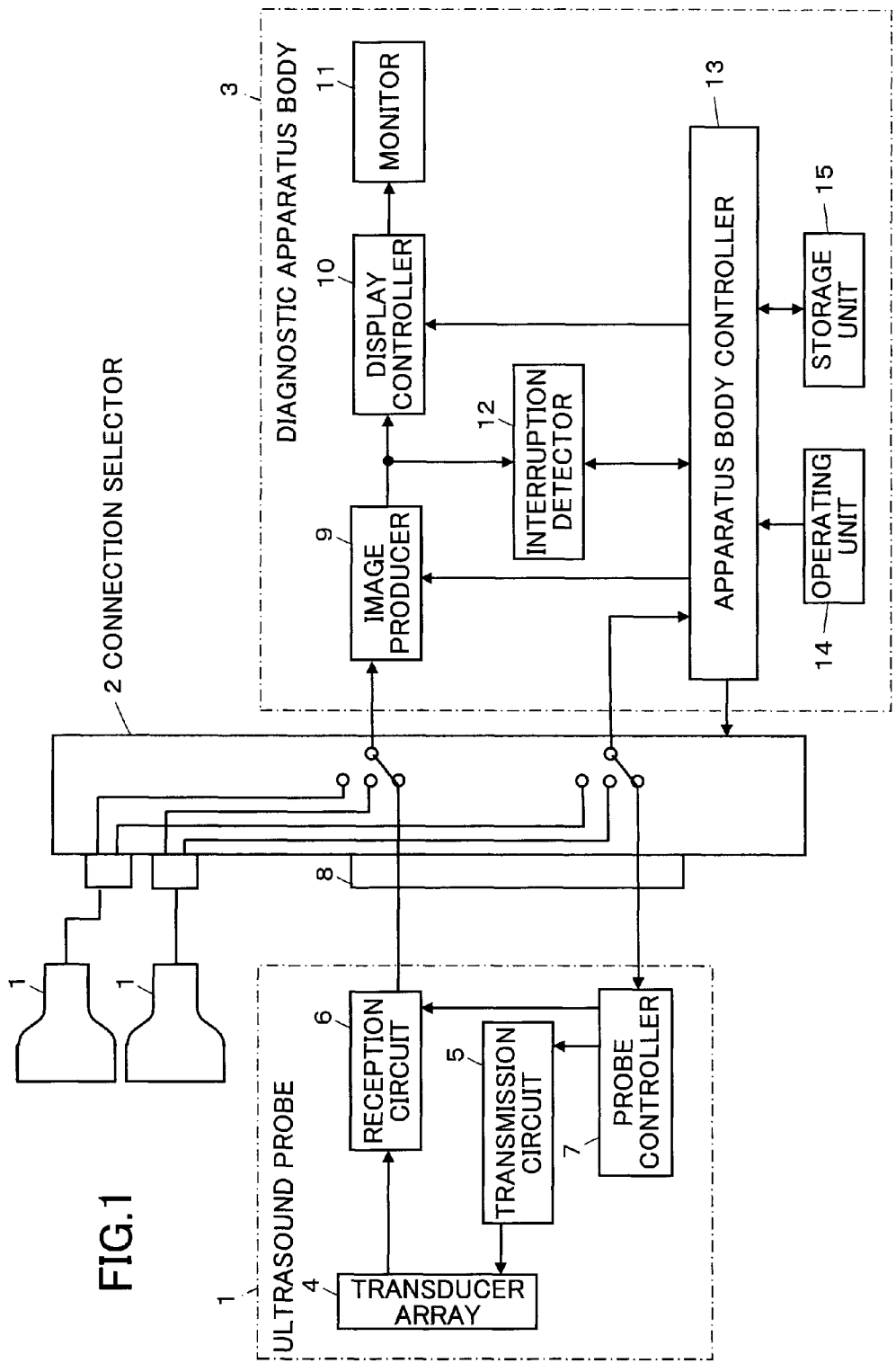
FIG. 1 is a block diagram illustrating a configuration of an ultrasound diagnostic apparatus according to Embodiment 1 of the invention.

FIG. 1 illustrates a configuration of an ultrasound diagnostic apparatus according to Embodiment 1 of the invention. The ultrasound diagnostic apparatus comprises a plurality of ultrasound probes 1 and a diagnostic apparatus body 3 that is electrically connected to one of the ultrasound probes 1 via a connection selector 2.

In each ultrasound probe, a one-dimensional or two-dimensional transducer array 4 is connected to a transmission circuit 5 and a reception circuit 6, which in turn are connected to a probe controller 7.

The transducer array 4 of each ultrasound probe 1 comprises a plurality of ultrasound transducers, each of which transmits ultrasonic waves according to a driving signal supplied from the transmission circuit 5 and receive ultrasonic echoes from a subject to output a reception signal. Each of the ultrasound transducers comprises a vibrator composed of a piezoelectric body and electrodes each provided on both ends of the piezoelectric body. The piezoelectric body is composed of, for example, a piezoelectric ceramic represented by a PZT (titanate zirconate lead), a polymeric piezoelectric device represented by PVDF (polyvinylidene fluoride), or a piezoelectric monochristal represented by PMN-PT (lead magnesium niobate lead titanate solid solution).

When the electrodes of each of the vibrators are supplied with a pulsed voltage or a continuous-wave voltage, the piezoelectric body expands and contracts to cause the vibrator to produce pulsed or continuous ultrasonic waves. These ultrasonic waves are combined to form an ultrasonic beam. Upon reception of propagating ultrasonic waves, each vibrator expands and contracts to produce an electric signal, which is then outputted as reception signal of the ultrasonic waves.

The transmission circuit 5 includes, for example, a plurality of pulsars and adjusts the delay amounts for driving signals based on a transmission delay pattern selected according to a control signal transmitted from the probe controller 7 so that the ultrasonic waves transmitted from a plurality of ultrasound transducers of the transducer array 4 form an ultrasonic beam, and supplies the ultrasound transducers with delay-adjusted driving signals.

The reception circuit 6 amplifies and A/D-converts the reception signals transmitted from the ultrasound transducers of the transducer array 4, and then performs reception focusing processing by providing the reception signals with respective delays according to the sound speed or sound speed distribution that is set based on a reception delay pattern selected according to the control signal transmitted from the probe controller 7 and adding up the reception signals. This reception focusing processing yields reception data (sound ray signals) having the ultrasonic echoes well focused.

The probe controller 7 controls various components of the ultrasound probe 1 according to control signals transmitted from the diagnostic apparatus body 3.

The connection selector 2 is connected to the ultrasound probes via a connector 8 and to the single diagnostic apparatus body 3. According to a control signal transmitted from the diagnostic apparatus body 3, the connection selector 2 switches the connection to connect the diagnostic apparatus body 3 to a single ultrasound probe 1 to be used for diagnosis among a plurality of ultrasound probes 1. The connection selector 2 may be constituted, for example, by a multi-transducer port system that switches the connection between the diagnostic apparatus body 3 and one of the ultrasound probes 1.

The diagnostic apparatus body 3 comprises an image producer 9 connected to the connection selector 2; the image producer 9 is connected in sequence to a display controller 10 and a monitor 11. The image producer 9 is also connected to an interruption detector 12. The image producer 9, the display controller 10, and the interruption detector 12 are connected to an apparatus body controller 13. The apparatus body controller 13 is connected to an operating unit 14 and a storage unit 15.

As the connection is switched by the connection selector 2, the reception circuit 6 of one ultrasound probe 1 is connected to the image producer 9 of the diagnostic apparatus body 3, and the probe controller 7 of the one ultrasound probe 1 is connected to the apparatus body controller 13 of the diagnostic apparatus body 3 The apparatus body controller 13 of the diagnostic apparatus body 3 is connected to the connection selector 2.

The image producer 9 of the diagnostic apparatus body 3 corrects attenuation in the reception data produced by the reception circuit 6 of the ultrasound probe 1 according to the distance, i.e., the depth at which the ultrasonic waves are reflected, and then performs envelope detection processing to produce a B mode image signal, which is tomographic image information on a tissue inside the subject's body. The image producer 9 converts the produced B mode image signal into an image signal compatible with the scanning method of an ordinary television signal (raster conversion), and, through various image processing as required including gradation processing, outputs a B mode image signal to the display controller 10.

The display controller 10 causes the monitor 11 to display an ultrasound diagnostic image according to the B mode image signal generated by the image producer 9.

The monitor 11 includes a display device such as an LCD, for example, and displays an ultrasound diagnostic image under the control of the display controller 10.

The interruption detector 12 detects interruption of ultrasound examination effected by the operator.

The apparatus body controller 13 controls the components of the ultrasound diagnostic apparatus according to the instructions entered by the operator using the operating unit 14.

The operating unit 14 is provided for the operator to perform input operations and may be composed of, for example, a keyboard, a mouse, a track ball, and/or a touch panel. By operating the operating unit 14, the operator can switch the connection in the connection selector 2 so that one ultrasound probe 1 to be used for diagnosis among the ultrasound probes 1 connected to the connection selector 2 is connected to the diagnostic apparatus body 3.

The storage unit 15 stores, for example, an operation program and may be constituted by, for example, a recording medium such as a hard disk, a flexible disk, an MO, an MT, a RAM, a CD-ROM, a DVD-ROM, an SD card, a CF card, or a USB memory, a server, or the like.

The image producer 9, the display controller 10, the interruption detector 12, and the apparatus body controller 13 are each constituted by a CPU and an operation program for causing the CPU to perform various kinds of processing; they may be each constituted by a digital circuit.

Figure 2:
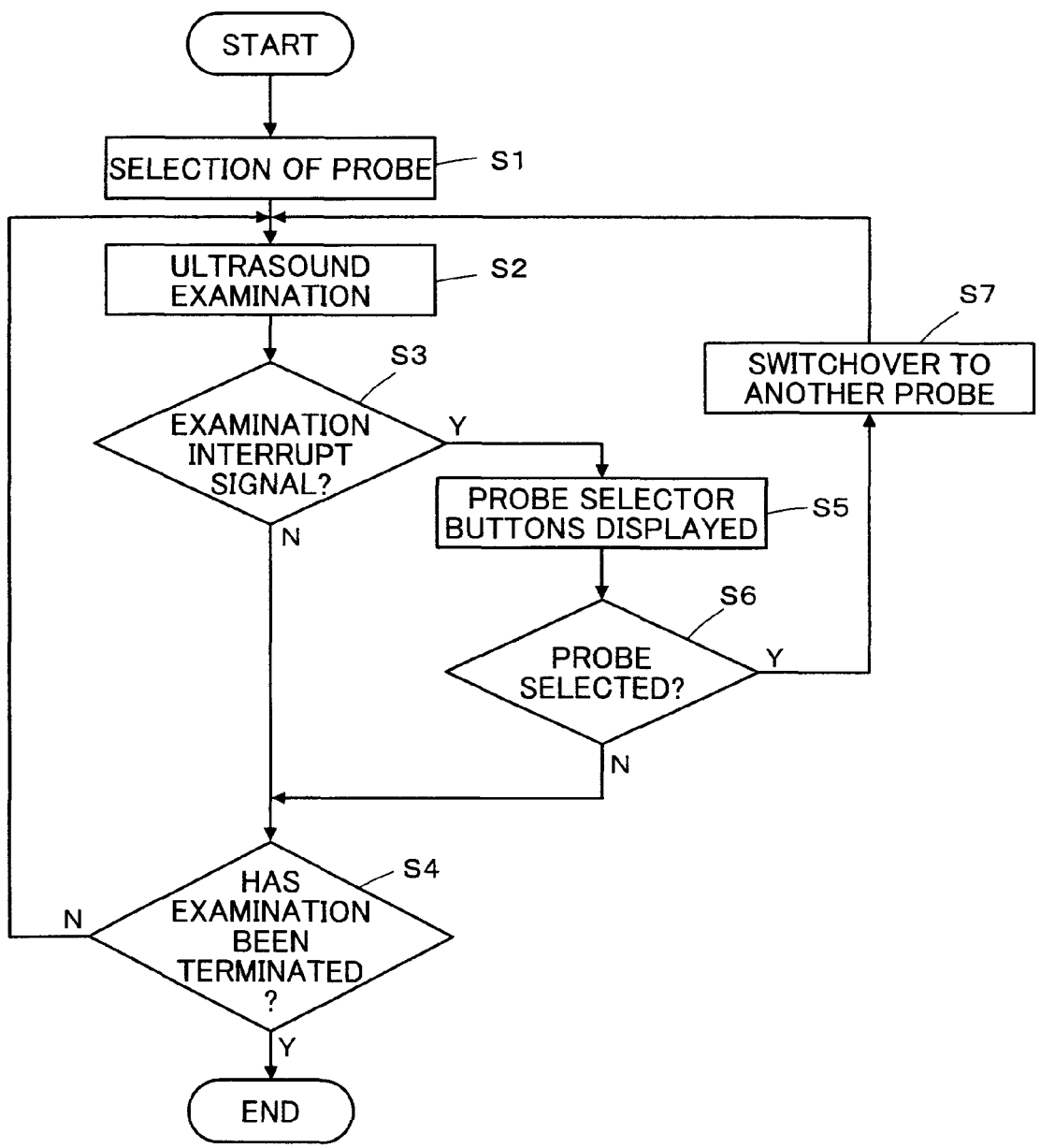
FIG. 2 is a flow chart illustrating the operation in Embodiment 1.

Next, the operation of Embodiment 1 will be described referring to the flowchart of FIG. 2.

First, the operator operates the operating unit 14 of the diagnostic apparatus body 3 to select an ultrasound probe P1 among a plurality of ultrasound probes 1, whereupon the apparatus body controller 13 controls the connection selector 2 to electrically connect the ultrasound probe P1 selected by the operator to the diagnostic apparatus body 3.

Upon connection of the ultrasound probe P1 and the diagnostic apparatus body 3, ultrasound examination is performed in step S2 such that a plurality of ultrasound transducers of the transducer array 4 transmit ultrasonic beams according to the driving signals supplied from the transmission circuit 5 of the ultrasound probe 1, while the ultrasound transducers having received ultrasound echoes from a subject output reception signals to the reception circuit 6 to produce reception data, whereupon the display controller 10 causes the monitor 11 to display, for example, the B mode image based on the ultrasound image signal produced by the image producer 9 of the diagnostic apparatus body 3. Unless the interruption detector 12 detects interruption effected by the operator of the ultrasound examination in step S3, the interrupt signal is not produced, proceeding to step S4 to wait until the operator gives an instruction to terminate the examination. When the instruction to terminate the examination is entered, a series of examination processing is terminated whereas when an instruction to continue the examination is entered, the procedure returns to step S2 to continue the ultrasound examination.

Figure 3:
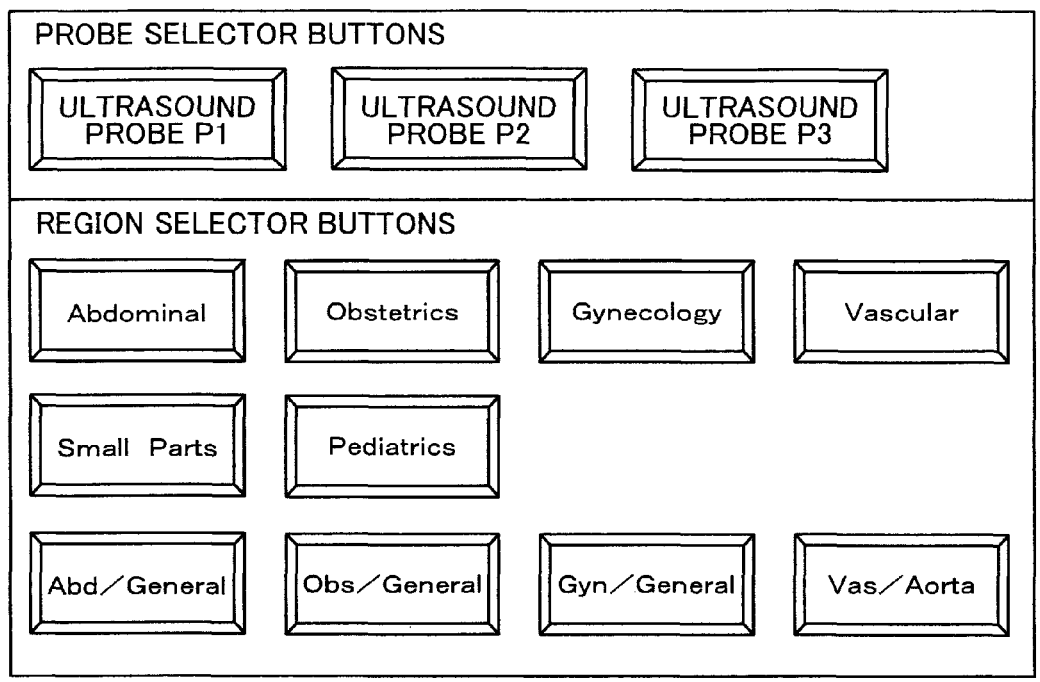
FIG. 3 illustrates a probe selection screen displayed on a screen.

When the interruption detector 12 detects interruption of the ultrasound examination in step S3 during the ultrasound examination in step S2, the interrupt signal is produced and supplied to the apparatus body controller 13. Upon receiving the interrupt signal from the interruption detector 12, the apparatus body controller 13 causes the monitor 11 to display the probe selection screen via the display controller 10 for the operator to select an ultrasound probe P2 to use next from among a plurality of ultrasound probes 1 in step S5. The probe selection screen may be configured as illustrated in FIG. 3, for example, by probe selector buttons showing, for example, the names of the ultrasound probes and may be displayed adjacent the region selector buttons for the operator to select a region to be diagnosed.

Subsequently, unless the operator selects the ultrasound probe P2 to use next from the probe selection screen displayed on the monitor 11 in step S6, judgment is made that the operator has no intention to replace the ultrasound probe P1 now in use with another ultrasound probe P2, waiting in step S4 until the operator gives an instruction to terminate the examination. When the operator selects the ultrasound probe P2 to use next from the probe selection screen displayed on the monitor 11 in step S6, the procedure proceeds to step S7, where the apparatus body controller 13 controls the connection selector 2 to break the connection between the ultrasound probe P1 used and the diagnostic apparatus body 3 while connecting the ultrasound probe P2 now selected by the operator to the diagnostic apparatus body 3 to switch between the ultrasound probes 1 for connection to the diagnostic apparatus body 3.

Thus, when the interruption detector 12 detects interruption of the ultrasound examination, the monitor 11 automatically displays the probe selection screen, so that the operator is saved the trouble of operating the operating unit 14 to cause the monitor 11 to display the probe selection screen each time the ultrasound probe P1 now in use is replaced with another ultrasound probe P2. Further, because the switchover of the connection between the diagnostic apparatus body 3 and one of the ultrasound probes 1 is effected by the operator directly operating the probe selection screen, the operator's intention can be infallibly incorporated into the judgment as to whether the connection is to be switched.

When the switchover of connection between the ultrasound probe 1 and the diagnostic apparatus body 3 has been completed, the ultrasound examination is resumed in step S2.

Figure 4:
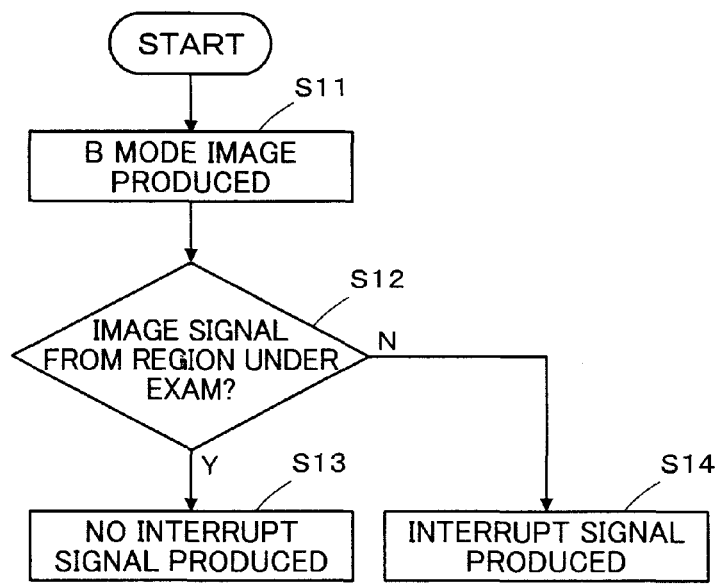
FIG. 4 is a flow chart representing the operation related to production of an interrupt signal in Embodiment 1.

The interrupt signal is produced by the interruption detector 12 in step S3 as illustrated in FIG. 4, for example. When the image producer 9 produces the B mode image in step S11 during the ultrasound examination in step S2, the procedure proceeds to step S12, where the interruption detector 12 judges whether the B mode image contains an image signal from a region of the subject to be diagnosed. When the image signal from the region to be diagnosed is detected, that is, when the reception signal for the ultrasonic echoes from the subject has been obtained, the interruption detector 12 judges that the operator has not interrupted the ultrasound examination and, in step S13, does not produce the interrupt signal. When, in step S12, the image signal from the region to be diagnosed is not detected, that is, when the reception signal for the ultrasonic echoes from the subject has not been obtained because, for example, the ultrasonic waves from the ultrasound probe P1 have been emitted into the air, the interruption detector 12 judges that the operator has interrupted the ultrasound examination and, in step S14, produces the interrupt signal.

Judgment made as to the interruption of the ultrasound examination based on the image signal from the subject ensures that the operator's intention is infallibly incorporated into the judgment.

Automatic display of the probe selection screen on the monitor 11 upon detection of interruption of the ultrasound examination reduces the workflow where the switchover between the ultrasound probe 1 and the diagnostic apparatus body 3 is related. Because the operator directly selects the ultrasound probe P2 to use next from the probe selection screen, the possibility of switchover to a connection not intended by the operator can be minimized.

Figure 5:
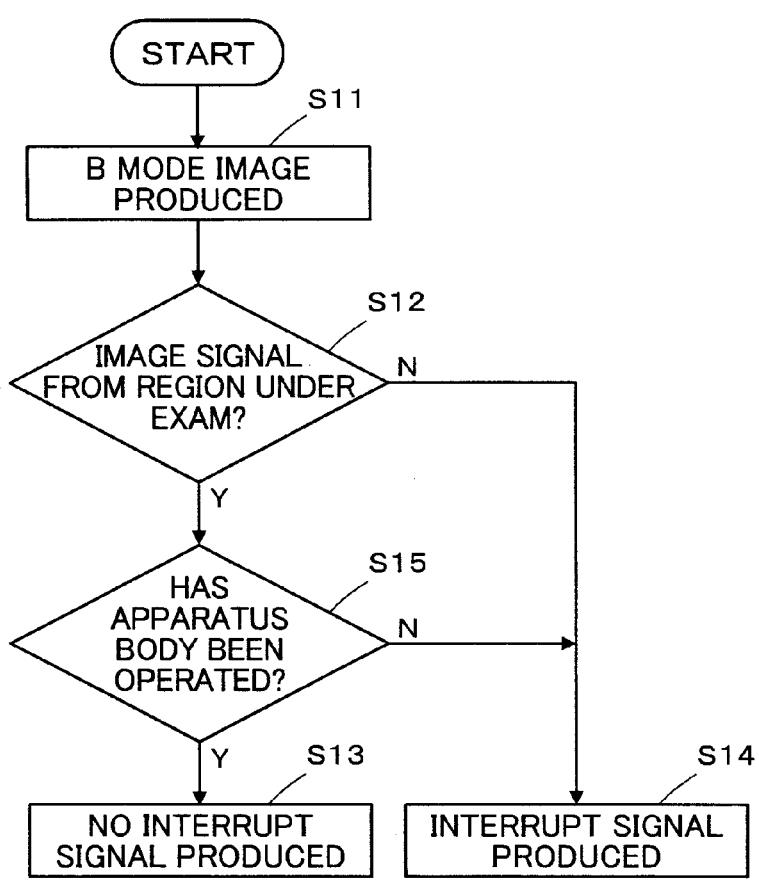
FIG. 5 is a flow chart representing the operation related to production of an interrupt signal in a variation of Embodiment 1.

The interrupt signal produced in step S3 by the interruption detector 12 may be alternatively produced upon judgment as to whether the operator has operated the diagnostic apparatus body 3 after judgment is made as to whether the B mode image contains an image signal from the region to be diagnosed in step S12 as illustrated in FIG. 5. When judgment is made that B mode image contains the image signal from the region to be diagnosed, judgment is made in step S15 as to whether the operator has operated the diagnostic apparatus body 3. When the diagnostic apparatus body 3 has been operated, the interruption detector 12 judges that the ultrasound examination has not been interrupted and does not produce the interrupt signal in step S13. When the apparatus body has not been operated in step S15, the interruption detector 12 detects interruption of the ultrasound examination and produces the interrupt signal in step S14.

Verifying whether the operator has operated the diagnostic apparatus body 3 in step S15 precludes the possibility of unnecessarily producing the interrupt signal when, for example, the operator only interrupts the operation of the ultrasound probe P1 in order to operate the diagnostic apparatus body 3, so that the operator's intention can be incorporated more reliably into the judgment as to the interruption of the ultrasound examination.

Embodiment 2

Figure 6:
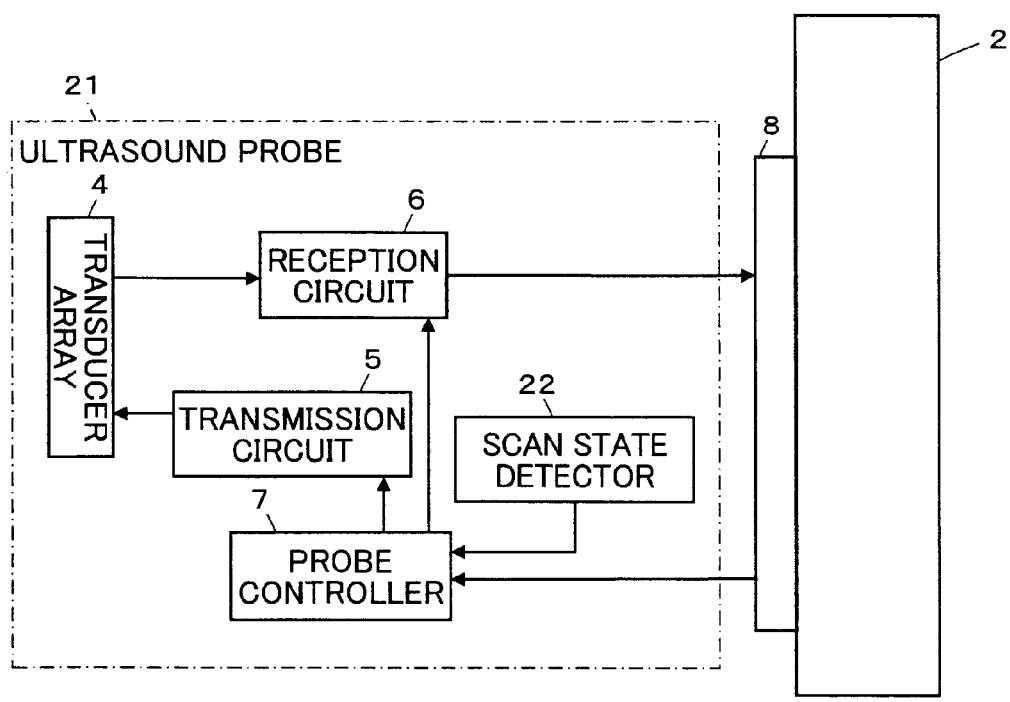
FIG. 6 is a block diagram illustrating a configuration of an ultrasound probe used in Embodiment 2.

FIG. 6 illustrates a configuration of an ultrasound probe 21 used in an ultrasound diagnostic apparatus according to Embodiment 2. The ultrasound probe 21 has the same components as the ultrasound probe 1 in Embodiment 1 illustrated in FIG. 1 except that a scan state detector 22 is provided and connected to the probe controller 7. The scan state detector 22 detects the scan state of the ultrasound probe 21 as operated by the operator and may be constituted, for example, by a gyro sensor that detects the movement of the ultrasound probe 21, a pressure sensor that detects the pressure with which the operator holds the ultrasound probe 21, or a temperature sensor that detects the body temperature of the operator touching the ultrasound probe 21.

The interrupt signal is produced by the interruption detector 12 as illustrated in FIG. 7 as in Embodiment 1; the B mode image is produced in step S11, and judgment is made in step S12 as to whether the B mode image contains an image signal from a region of the subject to be diagnosed. When the B mode image is judged to contain an image signal for the region to be diagnosed, the procedure proceeds to step S21, where judgment is made as to whether the operator is operating the ultrasound probe 21 to scan the subject based on the scan state of the ultrasound probe 21 detected by the scan state detector 22. When, for example, the scan state detector 22 detects a change in a movement of the ultrasound probe 21 equal to or greater than a given value, the interruption detector 12 judges that the operator is operating the ultrasound probe 21 to scan the subject, i.e., that the ultrasound examination has not been interrupted, and does not produce the interrupt signal in step S13. When, for example, the scan state detector 22 does not detect a change in a movement of the ultrasound probe 21 equal to or greater than a given value, the interruption detector 12 judges that the operator is not operating the ultrasound probe 21 to scan the subject, i.e., that the ultrasound examination has been interrupted, and produces the interrupt signal in step S14.

Verifying whether the operator is operating the ultrasound probe 21 in step S21 precludes the possibility of unnecessarily producing the interrupt signal when, for example, the operator only temporarily interrupts the operation of the ultrasound probe 21 in order to withdraw the ultrasound probe 21 from the subject and resume the examination, so that the operator's intention can be incorporated more reliably into the judgment as to the interruption of the ultrasound examination.

As illustrated in FIG. 8, the production of the interrupt signal may also be executed by judging whether the operator is operating the ultrasound probe 21 in step S22 upon production of the B mode image in step S11. When the scan state detector 22 senses that the ultrasound probe 21 is scanning the subject, the interruption detector 12 judges that the ultrasound examination has not been interrupted and does not produce the interrupt signal in step S13. When the scan state detector 22 judges that the ultrasound probe 21 is not scanning the subject, the interruption detector 12 detects interruption of the ultrasound examination and produces the interrupt signal in step S14.

Because judgment is made as to interruption of the ultrasound examination based on the scan state of the ultrasound probe 21, the operator's intention can be infallibly incorporated into the judgment.

What is claimed is:

1. An ultrasound diagnostic apparatus, comprising:
a plurality of ultrasound probes that transmit an ultrasonic beam toward a subject and receive ultrasonic echoes from the subject to produce reception data;
an apparatus body to which any one of the plurality of ultrasound probes is connected, and that produces an ultrasound image based on the reception data obtained by the one of the plurality of ultrasound probes connected to the apparatus body and displays the produced ultrasound image;
a connection selector that selectively switches a connection between the plurality of ultrasound probes and the apparatus body to connect one ultrasound probe among the plurality of ultrasound probes to be used for examination;
an operating unit that receives input from an operator to perform an input operation;
an interruption detector that detects interruption of the ultrasound probe connected to the apparatus body by the connection selector ultrasound examination without operation of the operating unit by the operator; and
a controller that causes the apparatus body to automatically display a selection screen for selecting one of the ultrasound probes to be subsequently used when the interruption detector detects interruption of the ultrasound probe connected to the apparatus body ultrasound examination,
wherein, when the operator selects via the operating unit one of the ultrasound probes from the displayed selection screen for subsequent use, the controller controls the connection selector to connect the selected ultrasound probe with the apparatus body.

2. The ultrasound diagnostic apparatus according to claim 1, wherein the interruption detector detects interruption of the ultrasound probe connected to the apparatus body when the reception data is not obtained.

3. The ultrasound diagnostic apparatus according to claim 2, wherein the interruption detector detects interruption of the ultrasound probe connected to the apparatus body when the operating unit is not being operated by the operator.

4. The ultrasound diagnostic apparatus according to claim 3, further comprising:
a scan state detector that detects a state in which the operator operates the ultrasound probe for scanning,
wherein the interruption detector detects interruption of the ultrasound probe connected to the apparatus body when the scan state detector detects that one of the ultrasound probes connected to the apparatus body is not being operated to scan the subject.

5. The ultrasound diagnostic apparatus according to claim 4, wherein the scan state detector includes one of a gyro sensor for detecting a movement of the one of the ultrasound probes connected to the apparatus body, a pressure sensor for detecting a pressure with which the operator holds the one of the ultrasound probes connected to the apparatus body, and a temperature sensor for detecting an body temperature of the operator touching the one of the ultrasound probes connected to the apparatus body.

6. The ultrasound diagnostic apparatus according to claim 2, further comprising:
a scan state detector that detects a state in which the operator operates the ultrasound probe for scanning,
wherein the interruption detector detects interruption of the ultrasound probe connected to the apparatus body when the scan state detector detects that one of the ultrasound probes connected to the apparatus body is not being operated to scan the subject.

7. The ultrasound diagnostic apparatus according to claim 6, wherein the scan state detector includes one of a gyro sensor for detecting a movement of the one of the ultrasound probes connected to the apparatus body, a pressure sensor for detecting a pressure with which the operator holds the one of the ultrasound probes connected to the apparatus body, and a temperature sensor for detecting an body temperature of the operator touching the one of the ultrasound probes connected to the apparatus body.

8. The ultrasound diagnostic apparatus according to claim 1, further comprising:
- a scan state detector that detects a state in which the operator operates the ultrasound probe for scanning,
- wherein the interruption detector detects interruption of the ultrasound probe connected to the apparatus body when the scan state detector detects that one of the ultrasound probes connected to the apparatus body is not being operated to scan the subject.

9. The ultrasound diagnostic apparatus according to claim 8, wherein the scan state detector includes one of a gyro sensor for detecting a movement of the one of the ultrasound probes connected to the apparatus body, a pressure sensor for detecting a pressure with which the operator holds the one of the ultrasound probes connected to the apparatus body, and a temperature sensor for detecting an body temperature of the operator touching the one of the ultrasound probes connected to the apparatus body.

10. An ultrasound image producing method, comprising the steps of:
- connecting one of a plurality of ultrasound probes used for examination to an apparatus body through a connection selector for selectively switching a connection between the ultrasound probes and the apparatus body;
- transmitting an ultrasonic beam from the one of the ultrasound probes connected to the apparatus body toward a subject;
- producing reception data by the one of the ultrasound probes connected to the apparatus body and having received ultrasonic echoes from the subject;
- producing an ultrasound image based on the produced reception data;
- displaying the produced ultrasound image;
- detecting interruption of the ultrasound probe connected to the apparatus body without an operator operating an operating unit;
- upon interruption of the ultrasound probe connected to the apparatus body being detected in said detecting step, automatically displaying a selection screen for selecting one of the ultrasound probes to be subsequently used; and
- controlling the connection selector to connect the selected ultrasound probe with the apparatus body when the operator selects one of the ultrasound probes to be subsequently used from the displayed selection screen.

11. The ultrasound image producing method according to claim 10, wherein the detecting step detects interruption of the ultrasound probe connected to the apparatus body by way of any of i) determining that reception data is not obtained from any of the ultrasound probes connected to the apparatus body, ii) determining that the operating unit is not being operated by the operator, and iii) determining that no ultrasound probes connected to the apparatus body are being operated to scan the subject.

* * * * *